(12) United States Patent
Jayaraman

(10) Patent No.: US 6,214,040 B1
(45) Date of Patent: Apr. 10, 2001

(54) SANDWICH STENT WITH SPIRALING BANDS ON AN OUTER SURFACE

(75) Inventor: Swaminathan Jayaraman, Fremont, CA (US)

(73) Assignee: Iowa-India Investments Company Limited (GB)

( * ) Notice: Subject to any disclaimer, the term of this patent is extended or adjusted under 35 U.S.C. 154(b) by 0 days.

(21) Appl. No.: 09/379,524

(22) Filed: Aug. 24, 1999

Related U.S. Application Data

(62) Division of application No. 08/954,188, filed on Oct. 20, 1997, now Pat. No. 5,980,565.

(51) Int. Cl.$^7$ ........................................................ A61F 2/06
(52) U.S. Cl. .................... 623/1.13; 623/1.18; 623/1.34; 600/36
(58) Field of Search .................... 623/1.13, 1.42, 623/1.45, 1.46, 1.34, 1.18; 600/36

(56) References Cited

U.S. PATENT DOCUMENTS

| | | | |
|---|---|---|---|
| 4,580,568 | * | 4/1986 | Gianturco ............................ 128/345 |
| 4,733,665 | * | 3/1988 | Palmaz ................................ 128/343 |
| 5,019,090 | * | 5/1991 | Pinchuk .............................. 623/1.15 |
| 5,100,429 | | 3/1992 | Sinofsky et al. . |
| 5,275,622 | | 1/1994 | Lazarus et al. . |
| 5,405,378 | | 4/1995 | Strecker . |
| 5,562,727 | | 10/1996 | Turk et al. . |
| 5,562,728 | | 10/1996 | Lazarus et al. . |
| 5,578,071 | | 11/1996 | Parodi . |
| 5,624,411 | * | 4/1997 | Tuch ..................................... 604/265 |
| 5,645,559 | | 7/1997 | Hachtman et al. . |
| 5,667,523 | | 9/1997 | Bynon et al. . |
| 5,693,088 | | 12/1997 | Lazarus . |
| 5,723,003 | | 3/1998 | Winston et al. . |
| 5,725,572 | | 3/1998 | Lam et al. . |
| 5,741,326 | | 4/1998 | Solovay . |
| 5,824,054 | * | 10/1998 | Khosravi et al. ................... 623/1.13 |
| 5,865,723 | * | 2/1999 | Love .................................... 600/36 |

* cited by examiner

Primary Examiner—David J. Isabella
Assistant Examiner—Choon P. Koh
(74) Attorney, Agent, or Firm—Larson & Larson, P.A.; James E. Larson

(57) ABSTRACT

A stent is made generally tubular and is initially formed in a collapsed configuration. A fabric cover is provided for the inner stent and is attached outside the stent at one or more desired locations. The fabric cover is larger in diameter than the diameter of the collapsed stent, however, when the stent is expanded through activation of the balloon catheter therewithin, the stent expands to closely conform to the interior walls of the fabric cover. The securement of the fabric cover or intermediate stent layer about the inner stent is accomplished through the use of a wire spiraling externally about the outer surface of the fabric cover to secure the fabric cover or intermediate stent layer about the inner stent. When the stent sandwich is expanded, the configuration of this spiraling wire permits it to expand as well and lie against the inner walls of the blood vessel at the desired location. The stent has spaced ends, each of which may be coated or otherwise provided with a radio-opaque material.

15 Claims, 3 Drawing Sheets

SANDWICH STENT WITH SPIRALING BANDS ON AN OUTER SURFACE

PRIOR APPLICATION

This application is a divisional U.S. Ser. No. 08/954,188, U.S. Pat. No. 5,980,565 filed on Oct. 20, 1997.

BACKGROUND OF THE INVENTION

1. Field of the Invention

The present invention relates to a stent. More particularly, it relates a sandwich stent which provides a mechanical barrier for prohibiting the growth of tissue through an artery implanted stent.

2. Description of the Prior art

In the prior art, stents are well known for use in minimally invasive surgery or interventional procedures for attaching to the inner walls of a blood vessel where a procedure such as a balloon angioplasty has been performed. Such prior art stents are essentially metallic scaffolds that are left in the arteries to prevent the arteries from collapsing back to their original form due to a phenomenon called elastic recoil. Such recoil can be common after the dilatation of a balloon.

Although the subject prior art stents have been generally successful in preventing elastic recoil, they have not been successful in the prevention of in stent restenosis. Such phenomenon occurs when tissue grows into and through the struts of the stent due to openings in the stent struts. The tissue is then permitted to grow into the lumen and reocclude the artery, whereby a balloon angioplasty procedure must be repeated.

In an effort to prohibit in stent restenosis, stents were provided with covering material. Such can be seen in U.S. Pat. No. 5,562,728 to Lazarus et al. wherein a helical wrap of ribbon is attached to a covering material; the attachment being only at the ends. U.S. Pat. No. 5,578,071 to Parodi et al. show a vascular graft that has two stents attached at the ends of the tubular conduit, where at one wire is provided and woven into a distal end, or lower end, of the graft, the wire permitting the distal end of the graft to conform to and sealingly engage within the artery of the patient.

When conveying a stent to its point of use, it is imperative that any covering material be secured about the stent in a secure and tight fashion to preclude the stent from being "hung up" in some area of the vascular system of the patient while it is being conveyed to the point of use. The prior art stents do not adequately secure the cover to the stent to prohibit such hang up. Further, the prior art devices have a very large profile that require being cut down by a surgeon and inserted into the body through a very large opening. Accordingly, minimally invasive surgery, in its strictest meaning, is not provided. Because of the large profile, the prior art devices are not useable in every area of the body, but only in larger arteries.

A stent is needed that overcomes the problems in the prior art. Such a stent needs to be low in profile yet provide the necessary mechanical barrier to prevent in stent restenosis. An improved means of securement is needed to prevent the covering material hang up. Further, providing such an improved stent with a low profile can be used in widespread applications and not be limited to large artery procedures.

SUMMARY OF THE INVENTION

The present invention relates to embodiments of a sandwich stent. The present invention includes the following interrelated objects, aspects and features:

(1) In a first aspect, an inner stent in accordance with the teachings of the present invention is made generally tubular and is initially formed in a collapsed configuration. A balloon catheter may be contained within the collapsed stent and inflation of the balloon catheter at the site of installation causes the stent to expand to its expanded configuration lying closely against the inner walls of the desired blood vessel.

(2) A cover is provided for the inner stent and is attached outside the stent at one or more desired locations. An internal diameter of the cover is equivalent to the size of the artery in which it is being introduced. Since the cover is attached to the inner stent, when the stent is expanded by the balloon catheter, the stent expands to the internal diameter of the cover which happens to be the diameter of the artery. Hence, the covered stent conforms to the interior wall of the artery positioning therewithin.

(3) The attachment of the cover to the inner stent may be accomplished in several ways. In one embodiment, the cover may be attached outside the inner stent at one linear location parallel to the axis of elongation of the stent. In an alternative embodiment, the cover may be attached concentrically about the inner stent and secured in that configuration by a series of sutures. In a further modification, the fabric cover may be attached around the inner stent non-concentrically through the use of suitable sutures.

(4) The cover, also comprising an intermediate stent layer, is suitably collapsed and pleated so that it closely surrounds the inner stent. The present invention contemplates two exemplary embodiments of securement means for securing the cover or intermediate stent layer about the inner stent. In a first alternative, one or more expansible clips are collapsed about the cover to secure it about the inner stent. When the entire stent sandwich is expanded, these clips expand as well and comprise stents themselves. The slow expansion of the clips facilitates the unpleating or unraveling of the cover. Without such clips, the cover could have several folds and crimps upon expansion, hence, a potential for hang up. The clips facilitate uniform expansion and also assist in maintaining cover integrity. In a second alternative, securement of the fabric cover or intermediate stent layer about the inner stent is accomplished through the use of a wire spiraling externally about the outer surface of the cover to secure the cover or intermediate stent layer about the inner stent. When the stent sandwich is expanded, the configuration of this spiraling wire permits it to expand as well and lie against the inner walls of the blood vessel at the desired location.

(5) The stent has spaced ends, each of which may be coated or otherwise provided with a radio-opaque material. A cardiologist or surgeon may insert the stent and view its progress through the vascular system of the patient with equipment such as, for example, an X-ray device to ensure that the stent is properly traveling toward the location of installation and is precisely located at its final destination.

Accordingly, it is a first object of the present invention to provide a sandwich stent.

It is a further object of the present invention to provide such a stent including an inner stent, an intermediate stent comprising a cover and an outer stent comprising securement means for securing the cover about the inner stent.

It is a still further object of the present invention to provide such a stent wherein the cover is secured about the inner stent from within the cover in any one of several ways.

It is a still further object of the present invention to provide such a sandwich stent wherein the cover is secured about the inner stent from the outside therefrom in one of a plurality of possible ways.

These and other objects, aspects and features of the present invention will be better understood from the following detailed description of the preferred embodiment when read in conjunction with the appended drawing figures.

SPECIFIC DESCRIPTION OF THE PREFERRED EMBODIMENTS

Figure 1:
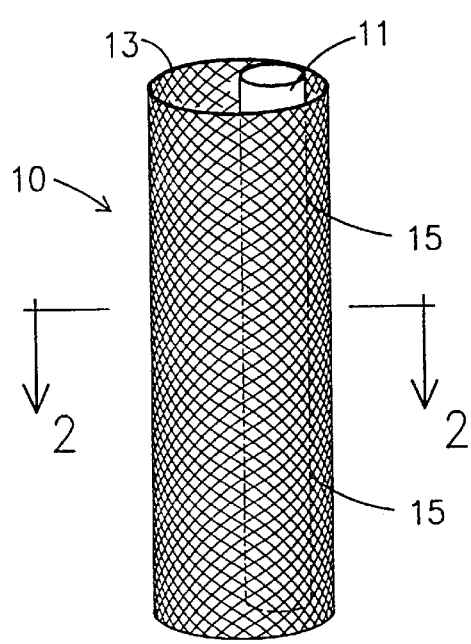
FIG. 1 shows a side perspective view of one embodiment of the inventive stent.

With reference, first, to FIG. 1, a stent is generally designated by the reference numeral 10 and is seen to include an inner stent 11 and a fabric cover or intermediate stent layer 13. The inner stent 11 is seen to be tubular in configuration and is shown in FIG. 1 in its collapsed configuration. In the preferred embodiment, the cover 13 is a woven fabric. But, other materials can be used. Further other forms of manufacturing can be used such as knitting, extruding, coextruding, braiding, interweaving, or interlocking. Cover 13 is coated or impregnated with a bioactive or bioinactive substance such as growth factors, growth factor inhibitors, anticoagulents and genetic therapeutic materials biologically or synthetically derived from gene matter. These substances are incorporated on the surface of fabric cover 13 either directly or indirectly using a combination of a controlled release agent which can be a synthetic biodegradable or non-biodegradable material. The substance also can be a biologically derived protein or liposome material.

Figure 2:
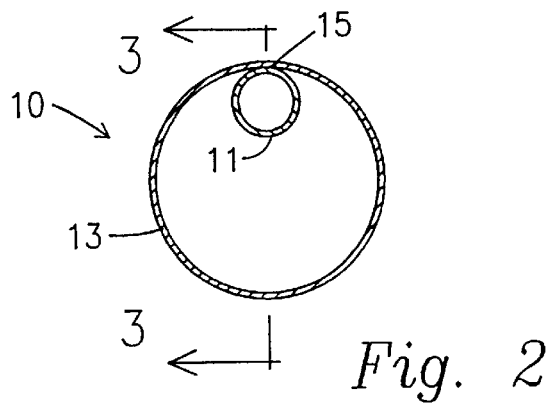
FIG. 2 shows a cross-sectional view along the line 2—2 of FIG. 1.

As seen in FIG. 2, the cover 13 is attached to the inner stent 11 at one linear location 15 on the inner stent. The reference numeral 15 is used in several locations in FIG. 1 to show the linear nature of the attachment location of the cover 13 on the inner stent 11. Attachment may be accomplished through any suitable means such as, for example, surgical staples, sutures, adhesion, imbedding within the walls, ultrasonic welding, or using an intermediate material to facilitate attachment. The preferred means of attachment is by sutures.

Figure 3:
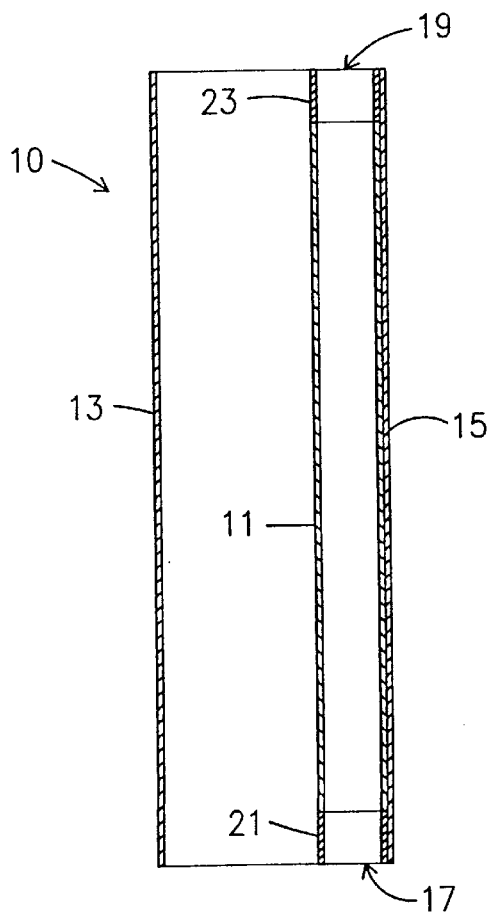
FIG. 3 shows a cross-sectional view along the line 3—3 of FIG. 2.

With reference to FIG. 3, the inner stent 11 includes ends 17 and 19. Bands 21 and 23 depict regions adjacent the ends 17 and 19, respectively, that are coated or otherwise provided with a radio-opaque material that shows up as a dark area impenetrable by X-rays. With the bands 21, 23 so applied, the location of the inner stent 11 is clearly visible within the vascular system of the patient by viewing it with an X-ray device.

Figure 4:
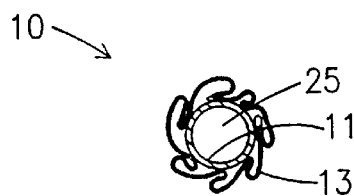
FIG. 4 shows a view similar to that of FIG. 2 but with the fabric stent cover folded and collapsed about the stent body.

As seen in FIG. 4, when the stent 10 is to be implanted within the patient, the cover 13 is folded and pleated in the manner shown in FIG. 4 so that it lies closely against the inner stent 11 in the collapsed state thereof providing the smallest possible cross-section to facilitate conveyance of the stent 10 with a balloon catheter 25 contained therein (FIG. 4).

The stent 10 may be conveyed to the site of installation using any desired well known method such as those described in U.S. Pat. Nos. 5,100,429 and 5,275,622.

The inner stent 11 may be made of any suitable material and the cover may be woven or otherwise fabricated.

Figure 5:
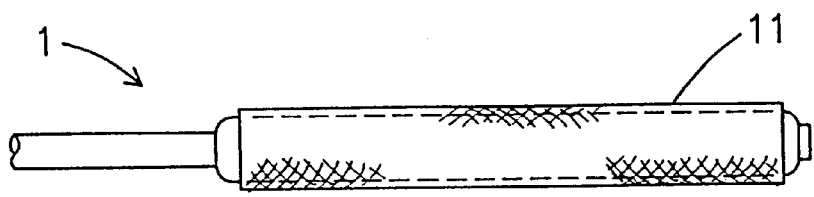
FIG. 5 shows the inner stent of FIGS. 1–4 with a delivery device such as a balloon catheter inserted therein.
Figure 6:
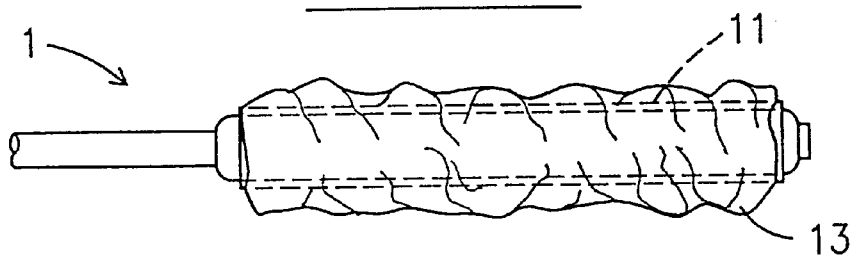
FIG. 6 shows the stent and delivery device of FIG. 5 with the cover or intermediate stent layer placed thereover.

With reference to FIG. 5, the inner stent 11 is seen with a delivery device 1 contained therein. With reference to FIG. 6, the cover 13 is seen to be installed over the inner stent 11 and comprises an intermediate stent layer.

Figure 7:
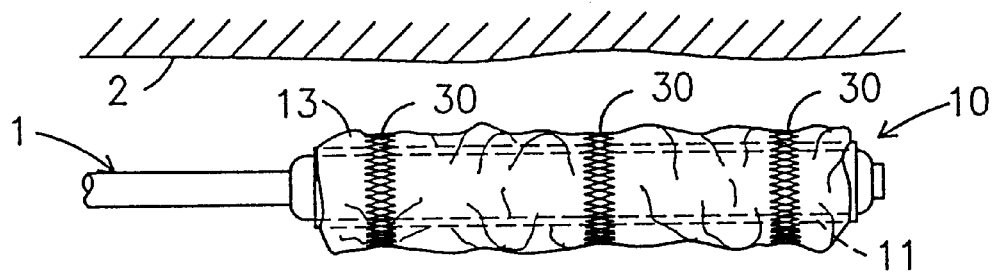
FIG. 7 shows the stent sandwich of FIG. 6 with the outer layer consisting of a plurality of narrow stent bands secured about the cover or intermediate stent layer as the entire stent assembly travels through a blood vessel.

FIG. 7 depicts, schematically, a blood vessel 2 in which the delivery device 1 has been inserted with the stent 10 placed thereover. The cover 13 is folded or otherwise pleated to closely conform to the outer surfaces of the inner stent 11 as also seen in FIG. 4. To secure the cover or intermediate stent layer 13 over the inner stent 11, a plurality of clips 30 are mounted over the cover 13 at spaced locations thereover and are in a collapsed configuration tightly holding the cover 13 over the inner stent 11. These clips 30 may, if desired, be made of a material such as NITINOL, a titanium-nickel alloy.

Figure 8:
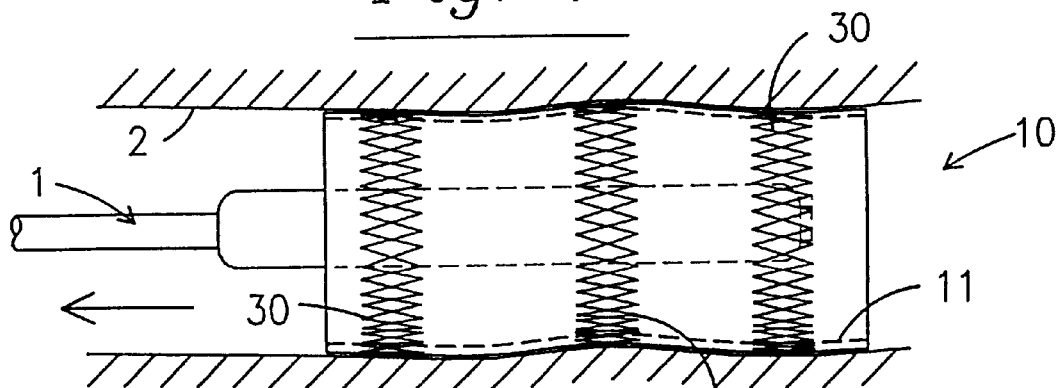
FIG. 8 shows the stent assembly expanded at a desired location within a blood vessel with the delivery device being removed.

With reference to FIG. 8, the delivery device 1 has expanded the stent 10 at the desired location within the blood vessel 2. As is clearly seen in FIG. 8, the clips 30 have expanded as has the cover 13 and inner stent 11 so that the entire sandwich is now securely mounted within the blood vessel 2 at the desired location.

Figure 9:
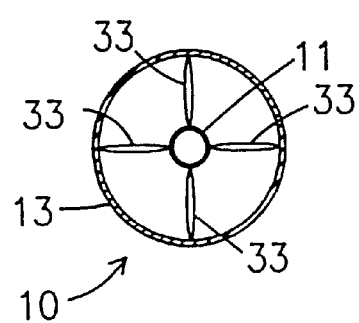
FIG. 9 shows a view similar to that of FIG. 2 but with an alternative means of securement of the cover about the inner stent.
Figure 10:
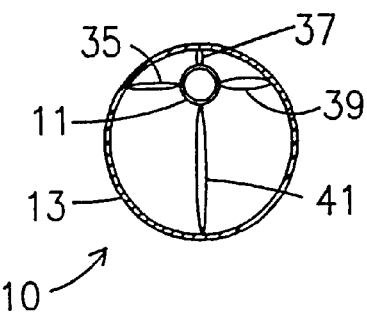
FIG. 10 shows a further modification as compared to the views of FIGS. 2 and 9.

With reference to FIGS. 9 and 10, two alternatives are depicted for securement of the cover 13 over the inner stent 11. In FIG. 9, the inner stent 11 is seen to be concentrically disposed within the cover 13. Sutures 33 of substantially equal length suspend the inner stent 11 concentrically within the cover 13. As should be understood, FIG. 9 depicts a cross-sectional view similar to that of FIG. 2. As such, a series of sutures 33 longitudinally spaced along the axis of elongation of the stent 10 are suitably provided.

With reference to FIG. 10, the inner stent 11 is seen non-concentrically supported within the cover 13. For this purpose, sutures 35, 37, 39 and 41 suspend the inner stent 11 non-concentrically within the fabric cover 13. As shown, the sutures 35 and 39 may be of similar lengths and the suture 37 its extremely short in length while the suture 41 is extremely lengthy. As is the case concerning the description in FIG. 9, FIG. 10 depicts a cross-sectional view similar to that of FIG. 2. As such, it should be understood that the sutures 35, 37, 39 and 41 depicted in FIG. 10 are merely representative of a series of sutures longitudinally spaced along the axis of elongation of the stent 10.

Figure 11:
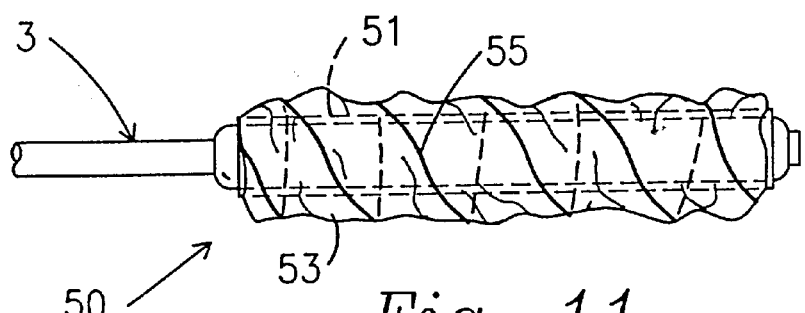
FIG. 11 shows a view similar to that of FIG. 7 but depicting an alternative outer securement means overlying the cover or intermediate stent layer.
Figure 12:
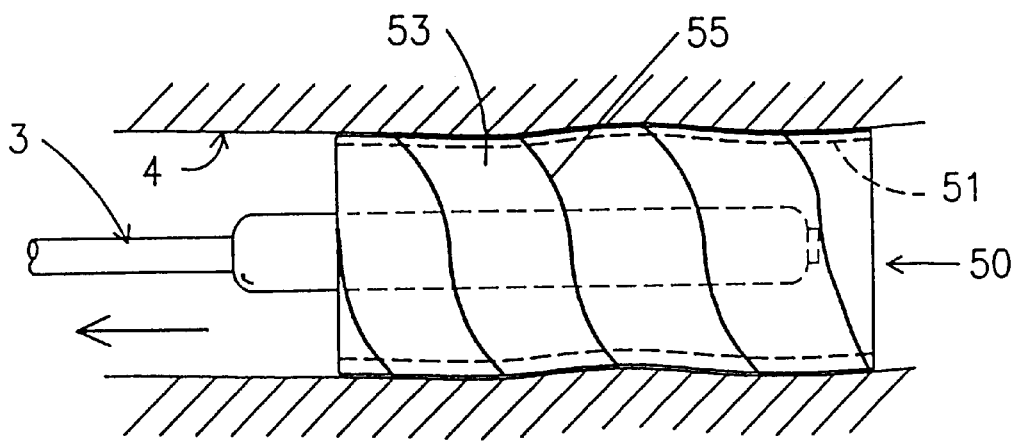
FIG. 12 shows a view similar to that of FIG. 8 but depicting the stent assembly of FIG. 11 as expanded within a blood vessel and with the delivery device being removed therefrom.

FIGS. 11 and 12 depict an alternative embodiment of the present invention including a stent 50 having an inner stent 51, a cover or intermediate stent layer 53 and an outer securement device or outer stent 55 consisting of a wire wound in a spiral fashion about the external surface of the cover 53 to secure the cover 53 about the inner stent 51. A delivery device 3 is also shown inserted within the inner stent 51. If desired, the wire 55 may be made of a material such as NITINOL, a titanium-nickel alloy. The spiraling wound wire 55 can be coated with a radio-opaque material for better visibility when positioning the sandwich stent of FIG. 11 within a patient's vessels.

FIG. 12 shows a blood vessel 4 in which the delivery device has delivered the stent 50 to a desired location of use and has expanded the stent 50 at that location. The cover 53 as well as the inner stent 51 and outer or securement device 55 are clearly depicted having been expanded into the installed location within the blood vessel 4.

In the embodiments of the present invention depicted in the drawing figures, the stents are shown as being balloon expandable. If so desired, the stent may also be self-expandable, thermal memory expandable, or a combination of the three. In one embodiment, the inside stent can be balloon expandable while the outside stent is self-expandable. Or, the inside stent can ne self-expandable, while the outside stent is thermally expandable. Yet, the inside stent can be thermally expandable while the outside stent can be balloon expandable.

The sandwich structure of the present invention causes a mutual interaction between the stent layers permitting uniform expansion. The clips illustrated in FIGS. 7 and 8 or, alternatively, the spiral wire illustrated in FIGS. 11 and 12, allow the cover to expand slowly and uniformly thereby maintaining integrity of the stent assembly. The inner stent 11 or 51 is continuous in structure while the cover and outer stents or clips are non-continuous. The elastic material of the inner stent may be made of a biological or synthetic material and is intended to provide a mechanical barrier. The degree of elasticity of this material may be greater than the degree of elasticity of the stents. The elastic deformation of the material is determined by the elastic deformation of the inner stent and the outer stent layers. If the inner stent is self-expandable, made of a material such as NITINOL, then the delivery device would not be a balloon. Rather, an "insertion catheter" would be used as the delivery mechanism.

As such, an invention has been disclosed in terms of preferred embodiments thereof which fulfill each and every one of the objects of the present invention as set forth hereinabove and provides a new and useful sandwich stent of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. A stent assembly comprising:

a) an inner continuous stent extending along the entire length of the assembly having spaced ends;

b) a fabric cover folded over the entire inner continuous stent in a collapsed state, the cover affixed only along a single longitudinal axis outside the inner, continuous stent to at least two points along the inner continuous stent;

c) the fabric cover conforming in an outer diameter to an inner diameter of an artery in which it will be positioned and an expansible outer stent in the form of a spiraling wire around the fabric cover to secure the fabric cover to the inner continuous stent;

d) the outer stent having a lesser longitudinal length than the inner stent; and e) an outer diameter of the inner stent being substantially equivalent to an inner diameter of the fabric cover when the inner stent is radially expanded.

2. The stent assembly of claim 1 wherein the inner continuous stent is tubular.

3. The stent assembly of claim 1 wherein the cover is affixed to the inner stent along a line parallel to a longitudinal axis of the inner stent.

4. The stent assembly of claim 1, wherein the spiraling wire consists of at least two spaced apart narrow bands.

5. The stent assembly according to claim 1, wherein the spiraling wire is made of a titanium nickel alloy.

6. A stent assembly comprising:

a) a tubular inner continuous stent having spaced ends;

b) a fabric cover folded over the entire inner continuous stent in a collapsed state the cover affixed outside the inner stent;

c) securement means consisting of an outer spiraling wire stent over the fabric cover; and d) the outer spiraling wire stent having a lessor longitudinal length than the tubular inner continuous stent.

7. The stent assembly of claim 6, wherein the outer spiraling wire stent has a plurality of spaced apart wire bands.

8. The stent assembly of claim 7, wherein the wire bands are spiraling closely about an outer surface of the fabric cover.

9. The stent assembly of claim 6, wherein the fabric cover has a diameter larger than a collapsed diameter of the inner stent.

10. The stent assembly of claim 6, wherein an end of the inner stent has a radio-opaque material thereon.

11. The stent assembly of claim 6, wherein the fabric cover is affixed to the inner stent along a line parallel to a longitudinal axis of the inner stent.

12. The stent assembly of claim 6, wherein the inner stent is secure non-concentrically within the fabric cover.

13. The stent assembly of claim 6 wherein the spiraling wire stent is coated with a radio-opaque matter.

14. The stent assembly of claim 6 wherein the fabric cover is coated or impregnated with a material selected from the group consisting of a growth factor, a growth factor inhibitor, an anticoagulant, a genetic therapeutic biologically derived from gene matter and a genetic therapeutic synthetically derived from gene matter.

15. The stent assembly of claim 14 wherein the coated or impregnated material is incorporated on the surface of the fabric cover with a controlled release agent.

* * * * *